US012721836B2

(12) United States Patent
Ganapathy et al.

(10) Patent No.: US 12,721,836 B2
(45) Date of Patent: Sep. 1, 2026

(54) ALPHA-METHYL-L-TRYPTOPHAN AS AN ORALLY ACTIVE DRUG FOR TREATING OR PREVENTING METABOLIC CONDITIONS

(71) Applicant: Texas Tech University System, Lubbock, TX (US)

(72) Inventors: Vadivel Ganapathy, Lubbock, TX (US); Sathish Sivaprakasam, Lubbock, TX (US); Yangzom D. Bhutia, Lubbock, TX (US); Sabarish Ramachandran, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 483 days.

(21) Appl. No.: 18/270,167

(22) PCT Filed: Dec. 23, 2021

(86) PCT No.: PCT/US2021/065129
§ 371 (c)(1),
(2) Date: Jun. 28, 2023

(87) PCT Pub. No.: WO2022/150203
PCT Pub. Date: Jul. 14, 2022

(65) Prior Publication Data

US 2024/0075010 A1 Mar. 7, 2024

Related U.S. Application Data

(60) Provisional application No. 63/134,230, filed on Jan. 6, 2021.

(51) Int. Cl.

| | |
|---|---|
| ***A61K 31/405*** | (2006.01) |
| ***A61K 9/00*** | (2006.01) |
| ***A61K 31/198*** | (2006.01) |
| ***A61P 1/16*** | (2006.01) |
| ***A61P 3/04*** | (2006.01) |
| ***A61P 3/10*** | (2006.01) |

(52) U.S. Cl.
CPC .......... *A61K 31/405* (2013.01); *A61K 9/0053* (2013.01); *A61K 31/198* (2013.01); *A61P 1/16* (2018.01); *A61P 3/04* (2018.01); *A61P 3/10* (2018.01)

(58) Field of Classification Search
CPC .................................................... A61K 31/405
See application file for complete search history.

(56) References Cited

U.S. PATENT DOCUMENTS

| | | | |
|---|---|---|---|
| 6,207,699 | B1 | 3/2001 | Rothman |
| 11,111,271 | B2 | 9/2021 | Cundy |
| 2009/0215895 | A1 | 8/2009 | Ferrante et al. |
| 2013/0101580 | A1 | 4/2013 | Oxenkrug et al. |
| 2013/0142815 | A1 | 6/2013 | Ganapathy |
| 2018/0369198 | A1 | 12/2018 | Inserm |
| 2020/0181197 | A1 | 6/2020 | Cundy et al. |

FOREIGN PATENT DOCUMENTS

| | | | |
|---|---|---|---|
| CA | 2088996 | A1 | 1/1992 |
| FI | 106197 | B | 12/2000 |

OTHER PUBLICATIONS

Sivaprakasam et al. Biochemical Journal, 2021, 478(7): 1347-1358.*

International Search Report and Written Opinion for PCT/US21/65129, mailed on Mar. 16, 2022.

Sankoff et al., "The Weight-Depressing Action of Alpha-Methyl-DL-Tryptophan in the Rat" Canadian Journal of Biochemistry and Physiology, vol. 40, No. 6 (Jun. 1962), p. 739- 747.

Filho et al., "IDO chronic immune activation and tryptophan metabolic pathway: a potential pathophysiological link between depression and obesity"; Progress in Neuro- Psychopharmacology and Biological Psychiatry, vol. 80, Part C (Jan. 2018), p. 234-249.

Sivaprakasam et al., "Alpha-Methyl-L-Tryptophan as a Weight-Loss Agent in Multiple Models of Obesity in Mice"; Biochemical Journal, vol. 478, Issue 7 (Apr. 2021), p. 1347-1358.

Stewart KD et al. Preference for pharmaceutical formulation and treatment process attributes. Patient Prefer Adherence. Jul. 2, 20167;10:1385-99. doi: 10.2147/PPA.S101821. PMID: 27528802; PMCID: PMC4970633.

* cited by examiner

*Primary Examiner* — Rei Tsang Shiao

(74) *Attorney, Agent, or Firm* — Farbang Amini; Shackelford, McKinley & Norton, LLP

(57) ABSTRACT

Embodiments of the present disclosure pertain to methods of treating or preventing a condition in a subject by administering to the subject a composition having alpha-methyl-L-tryptophan. In additional embodiments, the method further includes a step of instructing the subject to administer the composition in order to treat or prevent the condition in the subject. In some embodiments, the condition includes, without limitation, hyperglycemia, diet-induced diabetes, high-fat diet-induced diabetes, insulin resistance, metabolic syndrome, extra weight, obesity, hepatic steatosis, and combinations thereof. Additional embodiments of the present disclosure pertain to compositions for use in treating or preventing a condition in a subject. In some embodiments, the composition includes alpha-methyl-L-tryptophan.

19 Claims, 9 Drawing Sheets

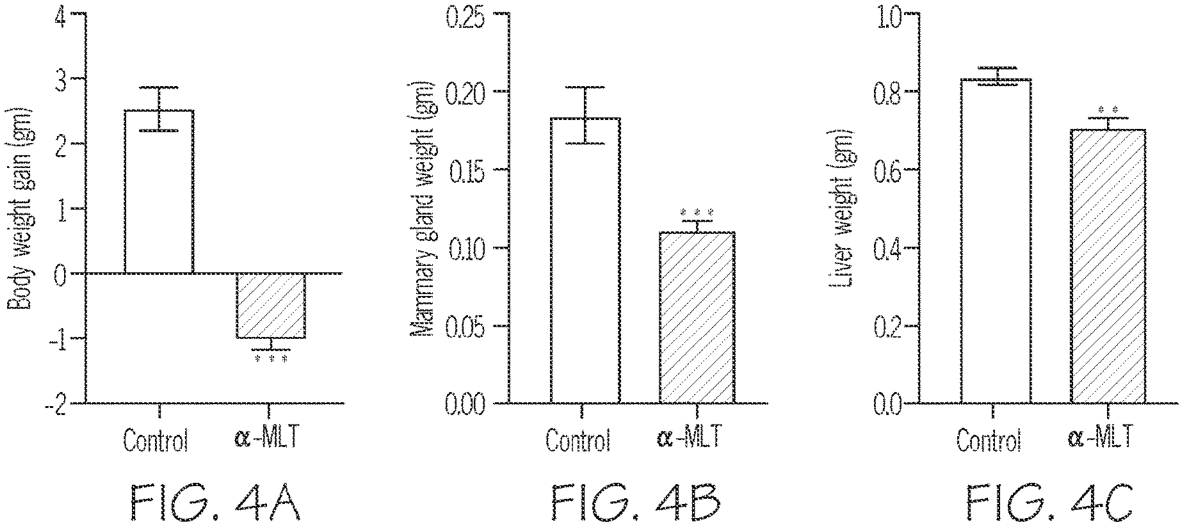
FIG. 4A
FIG. 4B
FIG. 4C
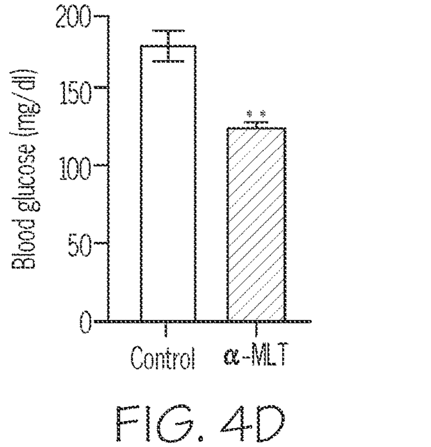
FIG. 4D
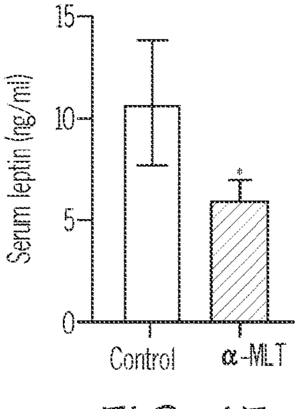
FIG. 4E

ALPHA-METHYL-L-TRYPTOPHAN AS AN ORALLY ACTIVE DRUG FOR TREATING OR PREVENTING METABOLIC CONDITIONS

CROSS-REFERENCE TO RELATED APPLICATIONS

This application claims priority to U.S. Provisional Patent Application No. 63/134,230, filed on Jan. 6, 2021. The entirety of the aforementioned application is incorporated herein by reference.

BACKGROUND

Being overweight or obese leads to several diseases, including cardiovascular diseases, type 2 diabetes, strokes, and certain types of cancer. Lifestyle changes such as eating fewer calories and/or burning more calories via exercise represent the most logical way to tackle this problem. However, it is not easy or effective to practice this strategy. Various embodiments of the present disclosure address the aforementioned need.

SUMMARY

In an embodiment, the present disclosure pertains to methods of treating or preventing a condition in a subject. In some embodiments, the method generally includes administering to the subject a composition having alpha-methyl-L-tryptophan. In some embodiments, the method further includes a step of instructing the subject to administer the composition in order to treat or prevent the condition in the subject. In some embodiments, the condition includes, without limitation, hyperglycemia, diet-induced diabetes, high-fat diet-induced diabetes, insulin resistance, metabolic syndrome, extra weight, obesity, hepatic steatosis, and combinations thereof. In some embodiments, the condition includes obesity or extra weight.

In an additional embodiment, the present disclosure pertains to compositions for use in treating or preventing a condition in a subject. In some embodiments, the composition includes alpha-methyl-L-tryptophan.

BRIEF DESCRIPTION OF THE DRAWINGS

FIG. 1A shows body weight gain in wild type (WT) male and Slc6a14$^{y/-}$ male mice on a normal diet (ND) and a high-fat diet (HFD) for 3 months. FIG. 1B shows body weight gain measured in wild type male mice on HFD without treatment (Control) or exposed to α-methyl-DL-tryptophan (α-MT, 2 mg/ml in drinking water) ad libitum for a week. FIG. 1C shows HFD-fed male Slc6a14$^{y/-}$ mice were exposed either to drinking water (Control) or α-methyl-D-tryptophan (α-MDT; 1 mg/ml) or α-methyl-L-tryptophan (α-MLT; 1 mg/ml) ad libitum for a week. At the end of the experiment, gain/loss in body weight was monitored. Data are means±S. E. M (N=5 mice/group). , p<0.01; *, p<0.001.

FIGS. 4A-E illustrate the effect of α-MLT on body weight and other biological parameters in wild type female mice fed with HFD. Wild type female mice were maintained on the HFD for 2 months prior to use in the experiment. Mice were then divided into two groups: control and treatment (α-MLT; 1 mg/ml in drinking water). Gain/loss in body weight was monitored for this 2-week period (FIG. 4A). At the end of experiment, blood was collected and mice were killed. Mammary gland and liver weights were measured (FIGS. 4B-C). Blood glucose levels (FIG. 4D) and serum leptin levels (FIG. 4E) were measured. Data means±S. E. M (N=5 mice/group). *, p<0.05; , p<0.01; *, p<0.001.

DETAILED DESCRIPTION

Figure 1A:
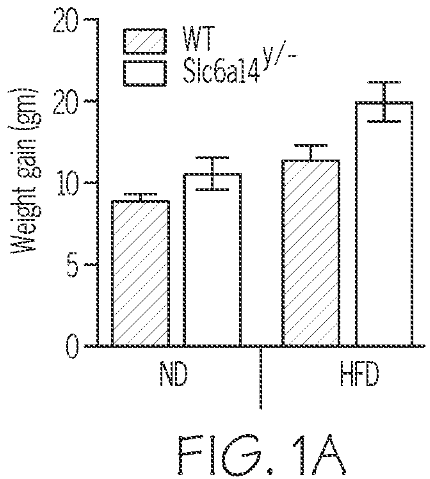
FIGS. 1A-C illustrate the effect of α-methyltryptophan (the DL-enantiomeric mixture and the individual D- and L-isomers) on body weight in wild type and Slc6a14-null male mice.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

The World Health Organization (WHO) estimates more than 1.9 billion adults 18 years or older are overweight or obese. Being overweight or obese leads to several diseases, including cardiovascular diseases, type 2 diabetes, strokes, and certain types of cancer. From a medical standpoint, disorders related to being overweight or obese are linked to more deaths worldwide than being underweight. Obesity (i.e., a body mass index≥30 kg/m$^2$) is a complex disorder arising from an imbalance between caloric intake and energy expenditure.

Simply put, obesity is a "disease of the mouth" (i.e., when people eat more than they expend or burn, they gain weight). What causes people to eat more and/or burn less may vary from patient to patient. Whatever the cause, obesity has become the fastest growing health concern worldwide. The problem does not stop just with the undesirable body mass index.

Rather, the problem forms the underlying cause for other health issues, including diabetes, metabolic syndrome, hypertension, myocardial infarction, stroke, cancer, and premature mortality. The sheer number of people suffering from this disorder and the broad range of associated metabolic complications come with a tremendous health care cost and consequent economic burden. There is a dire need for effective treatment strategies to address this major public concern. Sadly, currently available options are limited.

Currently available Food and Drug Administration (FDA)-approved anti-obesity drugs include a combination of phentermine and topiramate, a combination of naltrexone and bupropion, liraglutide, and orlistat. Amongst these, the first three are active in the brain. The first two are taken orally, and liraglutide by injection.

Alli, a lipase inhibitor, acts in the intestine by inhibiting the digestion of dietary fat. Liraglutide, a GLP1 receptor agonist, shows robust efficacy for weight loss, but as an injectable drug, it is less than desirable at least for some obese patients. Furthermore, Liraglutide is used for weight loss at a much higher dose than for diabetes, thus increasing the risk for cholelithiasis and possibly pancreatitis and pancreatic cancer.

Several other potential drug candidates for obesity are at various stages of development. This level of intense activity in pharmaceutical industries in the development of anti-obesity drugs highlights the dire need for a safe and effective pharmacotherapy to fight the obesity epidemic.

In sum, a need exists for more effective methods and compositions for treating or preventing various weight-related conditions in a subject, such as obesity and/or obesity-related conditions. Various embodiments of the present disclosure address the aforementioned need.

In some embodiments, the present disclosure pertains to methods of treating or preventing a condition in a subject. In some embodiments, the method generally includes administering to the subject a composition having alpha-methyl-L-tryptophan. In some embodiments, the method further includes a step of instructing the subject to administer the composition in order to treat or prevent the condition in the subject. Additionally, in some embodiments, the present disclosure pertains to compositions for use in treating or preventing a condition in a subject, where the compositions include alpha-methyl-L-tryptophan.

As set forth in further detail herein, the compositions and methods of the present disclosure can have numerous embodiments. For instance, the methods of the present disclosure can utilize compositions having numerous alpha-methyl-L-tryptophan forms, concentrations, and constituents. Furthermore, various methods may be utilized to treat or prevent different conditions in several types of subjects. Various methods may also be utilized to administer the compositions of the present disclosure to the subject.

Forms, Concentrations, and Constituents of Alpha-Methyl-L-Tryptophan

The present disclosure can utilize compositions having various forms of alpha-methyl-L-tryptophan. For instance, in some embodiments, the alpha-methyl-L-tryptophan in the composition is in an enantiomerically pure form. In some embodiments, the alpha-methyl-L-tryptophan in the composition is in racemic form. In some embodiments, the alpha-methyl-L-tryptophan in the composition is in a non-racemic form.

In some embodiments, the alpha-methyl-L-tryptophan in the composition is in an enantiomerically pure form or a non-racemic form. For instance, in some embodiments, the composition has D isomers of tryptophan at concentrations of less than 5 wt %. In some embodiments, the composition has D isomers of tryptophan at concentrations of less than 1 wt %. In some embodiments, the composition has D isomers of tryptophan at concentrations of less than 0.5 wt %. In some embodiments, the composition has D isomers of tryptophan at concentrations of less than 0.1 wt %. In some embodiments, the compositions lack D isomers of tryptophan. In some embodiments, the D isomer of tryptophan is pharmacologically inactive, but might be present at a low level when the pharmacologically active L isomer is synthesized and prepared.

In some embodiments, the composition is in the form of a liquid. In some embodiments, the liquid includes water. In some embodiments, the alpha-methyl-L-tryptophan is dissolved in the liquid. In some embodiments, the alpha-methyl-L-tryptophan is dissolved in the liquid at a concentration of at least 0.1 mg/ml. In some embodiments, the alpha-methyl-L-tryptophan is dissolved in the liquid at a concentration of at least 0.2 mg/ml. In some embodiments, the alpha-methyl-L-tryptophan is dissolved in the liquid at a concentration of at least 0.3 mg/ml. In some embodiments, the alpha-methyl-L-tryptophan is dissolved in the liquid at a concentration of at least 0.5 mg/ml. In some embodiments, the alpha-methyl-L-tryptophan is dissolved in the liquid at a concentration of at least 1 mg/ml.

In some embodiments, the alpha-methyl-L-tryptophan is at a concentration sufficient to treat or prevent a condition in a subject. In some embodiments, the alpha-methyl-L-tryptophan is at a concentration of at least about 5 wt %. In some embodiments, the alpha-methyl-L-tryptophan is at a concentration of at least about 10 wt %. In some embodiments, the alpha-methyl-L-tryptophan is at a concentration of at least about 15 wt %. In some embodiments, the alpha-methyl-L-tryptophan is at a concentration of at least about 25 wt %.

The compositions of the present disclosure can also having additional constituents. For instance, in some embodiments, the compositions of the present disclosure further include Carbidopa. In some embodiments, Carbidopa increases the half-life of alpha-methyl-L-tryptophan in circulation by preventing the metabolism of the latter.

In some embodiments, the compositions further include an active agent stabilizer. In some embodiments, the active stabilizer can include, without limitation, an anti-oxidant. In some embodiments, the anti-oxidant includes, without limitation, vitamin E, vitamin C, vitamin A, triglyceride, uric acid, glutathione, and combinations thereof.

In some embodiments, the compositions of the present disclosure can also include excipients. For instance, in some embodiments, the excipients include, without limitation, triglycerides, monosaccharides, disaccharides, polysaccharides, fibers, lipids, vitamins, minerals, phytochemicals, proteins, terpenoids, and combinations thereof.

In some embodiments, the compositions of the present disclosure are in the form of a pill. In some embodiments, the alpha-methyl-L-tryptophan is combined with Carbidopa in the composition to increase the efficacy of the former. As such, in some embodiments, both alpha-methyl-L-tryptophan and Carbidopa are combined into a single pill.

Conditions

The methods and compositions of the present disclosure can be utilized to treat or prevent numerous conditions. For instance, in some embodiments, the conditions include, without limitation, hyperglycemia, diet-induced diabetes, high-fat diet-induced diabetes, insulin resistance, metabolic syndrome, extra weight, obesity, hepatic steatosis, and combinations thereof. In some embodiments, the methods and compositions of the present disclosure can be utilized to treat or prevent obesity, extra weight, or weight gain in a subject.

In some embodiments, the methods and compositions of the present disclosure can be utilized to treat or prevent extra weight in a subject. In some embodiments, the methods and compositions of the present disclosure can be utilized to treat obesity in a subject. In some embodiments, obesity is defined by a body mass index of 30 $kg/m^2$ or higher.

Mechanisms of Action

Without being bound by theory, the compositions of the present disclosure can treat or prevent conditions in a subject through various mechanisms of action. For instance, in some embodiments, the compositions of the present disclosure act by reducing food intake in the subject.

In some embodiments, the compositions of the present disclosure act by conversion of alpha-methyl-L-tryptophan into alpha-methylserotonin in the brain. In some embodiments, the alpha-methylserotonin functions as a satiety signal. In some embodiments, the compositions of the present disclosure act by improving glucose tolerance, improving insulin sensitivity, decreasing markers of inflammation, and combinations thereof.

In some embodiments, combining alpha-methyl-L-tryptophan with Carbidopa prevents metabolism of the former outside the brain so that more of the former is available to the brain where it is converted into the satiety-inducing signal alpha-methylserotonin. Carbidopa does not enter the brain and therefore has no effect on the metabolism of alpha-methyl-L-tryptophan within the brain.

Subjects

As set forth in further detail herein, the compositions of the present disclosure can be administered to various subjects. For instance, in some embodiments, the subject is a mammal. In some embodiments, the subject is a human being. In some embodiments, the subject is suffering from a condition. In some embodiments, the subject is vulnerable to a condition. In some embodiments, the subject is obese. In some embodiments, the subject has a genetic predisposition to obesity. In some embodiments, the subject has extra weight. In some embodiments, the subject is desirous of losing weight.

Administration

The compositions of the present disclosure can be administered to subjects in various manners in order to treat or prevent a condition. For instance, in some embodiments, the administering includes, without limitation, intravenous administration, intramuscular administration, intradermal administration, intraperitoneal administration, subcutaneous administration, spray-based administration, aerosol-based administration, in ovo administration, oral administration, intraocular administration, intratracheal administration, intranasal administration, inhalational administration, and combinations thereof.

In some embodiments, the administration occurs by oral administration. In some embodiments, the orally administered composition is in liquid form. In some embodiments, the alpha-methyl-L-tryptophan in the liquid composition is in a non-racemic form.

In some embodiments, the compositions of the present disclosure can be utilized to treat a condition. In some embodiments, the compositions of the present disclosure can be utilized to prevent a condition.

The alpha-methyl-L-tryptophan in the compositions of the present disclosure may be administered to subjects at various concentrations. For instance, in some embodiments, the alpha-methyl-L-tryptophan may be administered at a concentration of at least 0.1 mg/g body weight/day. In some embodiments, the alpha-methyl-L-tryptophan may be administered at a concentration of at least 0.2 mg/g body weight/day. In some embodiments, the alpha-methyl-L-tryptophan may be administered at a concentration of at least 0.3 mg/g body weight/day. In some embodiments, the alpha-methyl-L-tryptophan may be administered at a concentration of at least 0.4 mg/g body weight/day. In some embodiments, the alpha-methyl-L-tryptophan may be administered at a concentration of at least 0.5 mg/g body weight/day.

The administration of the compositions of the present disclosure to subjects can have various effects. For instance, in some embodiments, the administration results in weight reduction in a subject. In some embodiments, the weight reduction represents at least a 5% reduction in the subject's weight after 4 weeks of daily administration. In some embodiments, the weight reduction represents at least a 10% reduction in the subject's weight after 4 weeks of daily administration. In some embodiments, the weight reduction represents at least a 15% reduction in the subject's weight after 4 weeks of daily administration. In some embodiments, the weight reduction represents at least a 20% reduction in the subject's weight after 4 weeks of daily administration.

In some embodiments, the administration results in reduction of abdominal fat in a subject. In some embodiments, the reduction of abdominal fat represents at least a 5% reduction in the subject's abdominal fat after 4 weeks of daily administration. In some embodiments, the reduction of abdominal fat represents at least a 10% reduction in the subject's abdominal fat after 4 weeks of daily administration. In some embodiments, the reduction of abdominal fat represents at least a 20% reduction in the subject's abdominal fat after 4 weeks of daily administration.

In some embodiments, the administration results in reduction of liver weight in a subject. In some embodiments, the reduction of liver weight represents at least a 5% reduction in the subject's liver weight after 4 weeks of daily administration. In some embodiments, the reduction of liver weight represents at least a 10% reduction in the subject's liver weight after 4 weeks of daily administration. In some embodiments, the reduction of liver weight represents at least a 20% reduction in the subject's liver weight after 4 weeks of daily administration. In some embodiments, the reduction of liver weight represents at least a 30% reduction in the subject's liver weight after 4 weeks of daily administration. In some embodiments, the reduction of liver weight represents at least a 50% reduction in the subject's weight after 4 weeks of daily administration.

In some embodiments, the administration results in reduction of blood cholesterol levels in a subject. In some embodiments, the reduction of blood cholesterol levels represents at least a 5% reduction in the subject's blood cholesterol levels after 4 weeks of daily administration. In some embodiments, the reduction of blood cholesterol levels represents at least a 10% reduction in the subject's blood cholesterol levels after 4 weeks of daily administration. In some embodiments, the reduction of blood cholesterol levels represents at least a 15% reduction in the subject's blood cholesterol levels after 4 weeks of daily administration. In some embodiments, the reduction of blood cholesterol levels represents at least a 20% reduction in the subject's blood cholesterol levels after 4 weeks of daily administration. In some embodiments, the reduction of blood cholesterol levels represents at least a 25% reduction in the subject's blood cholesterol levels after 4 weeks of daily administration. In some embodiments, the reduction of blood cholesterol levels represents at least a 30% reduction in the subject's blood cholesterol levels after 4 weeks of daily administration. In some embodiments, the reduction of blood cholesterol levels represents at least a 40% reduction in the subject's blood cholesterol levels after 4 weeks of daily administration. In some embodiments, the reduction of blood cholesterol levels represents at least a 50% reduction in the subject's blood cholesterol levels after 4 weeks of daily administration.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. α-Methyl-L-Tryptophan as a Weight-Loss Agent in Multiple Models of Obesity in Mice In this Example, Applicant demonstrates that, α-Methyl-L-tryptophan, a tryptophan derivative, functions as an effective, orally active, and freely reversible weight-reducing agent in multiple models of obesity in mice. The observed decrease in body weight is associated with decreased food intake and with reversal of obesity-related insulin resistance and fatty liver.

Currently, α-Methyl-L-tryptophan (α-MLT) is in use as a tracer in its $^{11}$C-labeled form to monitor the health of serotonergic neurons in humans. In this Example, Applicant found that this compound functions as an effective weight-loss agent at pharmacological doses in multiple models of obesity in mice. The drug was able to reduce the body weight when given orally in drinking water (1 mg/ml) in three different models of obesity: normal mice on high-fat diet, Slc6a14-null mice on high-fat diet, and oblob mice on normal diet. Only the L-enantiomer (α-MLT) was active while the D-enantiomer (α-MDT) had negligible activity. The weight-loss effect was freely reversible, with the weight gain resuming soon after the withdrawal of the drug. All three models of obesity were associated with hyperglycemia, insulin resistance, and hepatic steatosis; α-MLT reversed these features. There was a decrease in food intake in the treatment group. Mice on a high-fat diet showed decreased cholesterol and protein in the serum when treated with α-MLT. There was, however, no evidence of liver and kidney dysfunction. Plasma amino acid profile indicated a significant decrease in the levels of specific amino acids, including tryptophan; but the levels of arginine were increased. Applicant concludes that α-MLT is an effective, reversible, and orally active drug for the treatment of obesity and metabolic syndrome.

Example 1.1. Animals

C57B16 mice and oblob (leptin-deficient) mice were from Jackson Laboratories (Bar Harbor, ME). Slc6a14-null mice (Slc6a14$^{y/-}$ males and Slc6a14$^{-/-}$ females) on C57BU/6 background were generated in Applicant's lab and have been used to assess the role of this transporter in breast cancer and colon cancer. Mice had free access to water and diet ad libitum. Age- and gender-matched mice were used in control groups (no treatment). Mice were fed a normal diet (ND) (50 IF/6F 5V5R, Labdiet, St. Louis, MO) or a high-fat diet (HFD; 55% calorie from fat) (TD93075; Teklad diets, Madison, WI). The protocol was approved by the Institutional Animal Care and Use Committee of the Texas Tech University Health Sciences Center, Lubbock, TX, USA (IACUC approval number: 15002 for breeding protocol and 18005 for experimental protocol).

Example 1.2. Intraperitoneal Glucose Tolerance Test (GTT)

Intraperitoneal GTT was done in mice fasted for 4 h. Blood glucose was determined using the TRUE track blood glucose monitor (Trividia Health Inc, Fort Lauderdale, FL) at 0, 15, 30, 60, 90 and 120 min after i.p. injection of glucose (2 g/kg body weight).

Example 1.3. Serum Metabolic Panel Analysis

At the end of the experiment, mice were fasted for 4 h, and blood was collected via orbital sinus using local anesthesia proparacaine. Serum was prepared by centrifugation of the clotted blood, and used for metabolic panel. This was done at our Laboratory Animal Resources Center.

Example 1.4. Histology and Assessment of Steatosis in Liver

Liver tissue was excised and weighed immediately, snap-frozen in liquid nitrogen, and stored at −80° C. For Oil-red-O (ORO) staining, tissues were OCT embedded, frozen at −20° C., and cut, followed by staining. Slides made from formalin-fixed, paraffin-embedded liver blocks were stained with hematoxylin and eosin (H & E).

Example 1.5. Leptin Assay

Animals were fasted for 4 h and blood was collected as described above. Blood samples were centrifuged at 1500×g for 20 min and the serum samples were collected and kept at −80° C. until analyzed. Leptin was measured using the mouse/rat Quantikine ELISA kit (MOB00B, R & D Systems, MN).

Example 1.6. Amino Acid Analysis

Plasma samples were used for the determination of amino acids at the Molecular Structural Facility (Genome Center, University of California, Davis, CA) with Hitachi-8900 ion-exchange chromatography amino acid analyzer.

Example 1.7. Statistical Analyses

Statistical analysis was performed with a two-tailed, paired Student's t-test for single comparison and a p value<0.05 was considered statistically significant. Data are given as means±SEM.

Example 1.8. Weight-Reducing Effect of α-Methyltryptophan

Due to a connection between SLC6A14 and obesity in humans, Applicant monitored the body weight in wild type and Slc6a14-null mice. Applicant found that Slc6a14-null male mice became obese, but only when fed a high-fat diet (FIG. 1A). There was a little, but not significant, change in body weight when fed a normal diet (FIG. 1A).

Figure 1B:
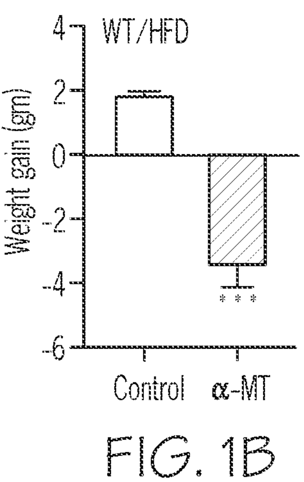

Administration of α-methyltryptophan to wild type mice on a high-fat diet would make the mice gain more weight as we found in Slc6a14-null male mice. The results turned out to be quite the opposite. When exposed to the drug for 1 week (2 mg/ml in drinking water; DL-enantiomeric mixture, α-MT), untreated wild type male mice on a high-fat diet gained weight whereas mice exposed to the drug lost weight (FIG. 1B). Since the deletion of Slc6a14 increased the weight gain whereas administration of α-MT to wild type mice decreased the weight gain, the effect of the drug on the body weight has little to do with its ability to block the transporter.

Example 1.9. Identification of the L-Isomer (α-Methyl-L-Tryptophan. α-MLT) as the Active Form for the Weight-Reducing Effect Next, Applicant aimed to determine which isomer in the enantiomeric mixture of α-methyltryptophan elicited a weight-reducing effect. For this, Applicant used the Slc6a14-null male mice on a high-fat diet as a model of obesity. Applicant selected this mouse model of obesity for initial experiments because the weight-reducing effect of α-MT is independent of what the drug does to the transport function of Slc6a14.

Figure 1C:
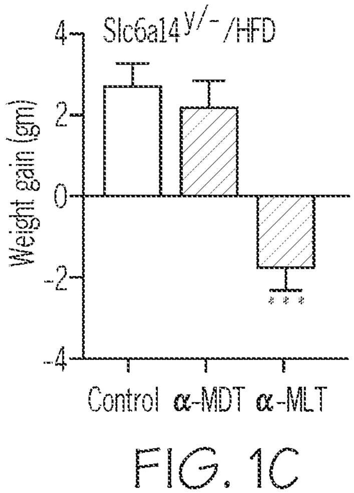

Applicant administered the D- and L-isomers separately to these mice on a high-fat diet at a dose of 1 mg/ml in drinking water for one week. Only the L-isomer (α-MLT) was active as a weight-reducing agent while the D-isomer (α-MDT) had negligible effect (FIG. 1C). This is the first time that the weight-reducing effect of α-methyltryptophan is being assigned specifically to the L-isomer.

Example 1.10. Effect of α-MLT on Body Weight in Other Models of Obesity in Mice

Figure 2A:
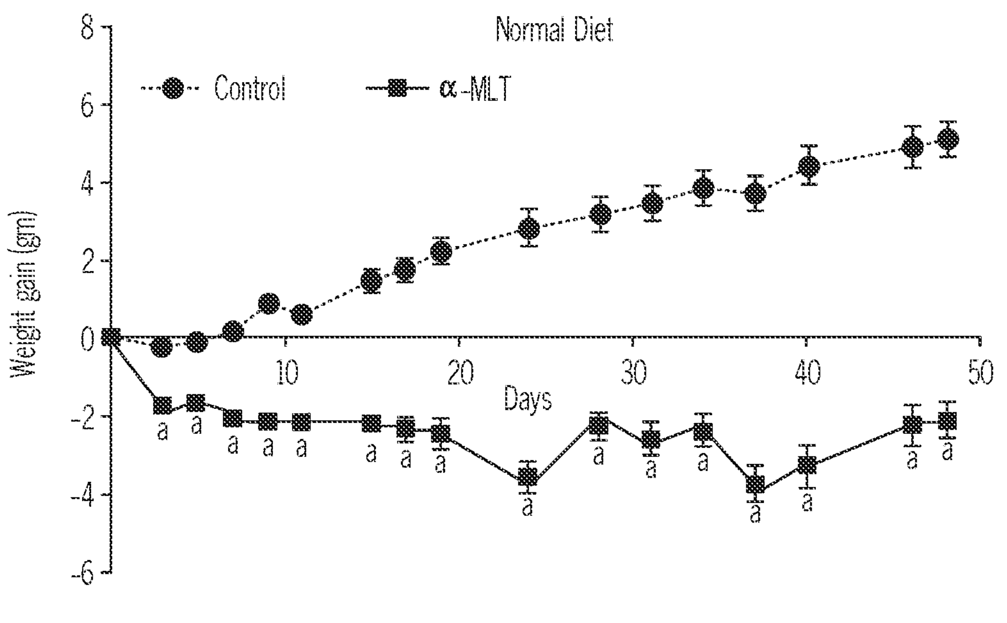
FIGS. 2A-D show weight-loss effect of α-MLT in wild type mice fed a normal diet or a high-fat diet and the consequences of the treatment on blood glucose and serum leptin levels. Wild type mice (males) fed with ND (FIGS. 2A and 2C) or HFD (FIGS. 2B and 2D) were subjected to drinking water alone or to α-MLT (1 mg/ml) in drinking water. The body weight was measured twice a week (FIGS. 2A-2B). At end of the 4-week period, blood was collected after 4-h fasting to measure blood glucose and leptin levels (FIGS. 2C-D). Data are means±S. E. M (N=5 mice/group). , p<0.01; *, p<0.001; a, p<0.001 compared to body weight in untreated control; b, p<0.001 compared to body weight at the time of drug withdrawal.
Figure 2B:
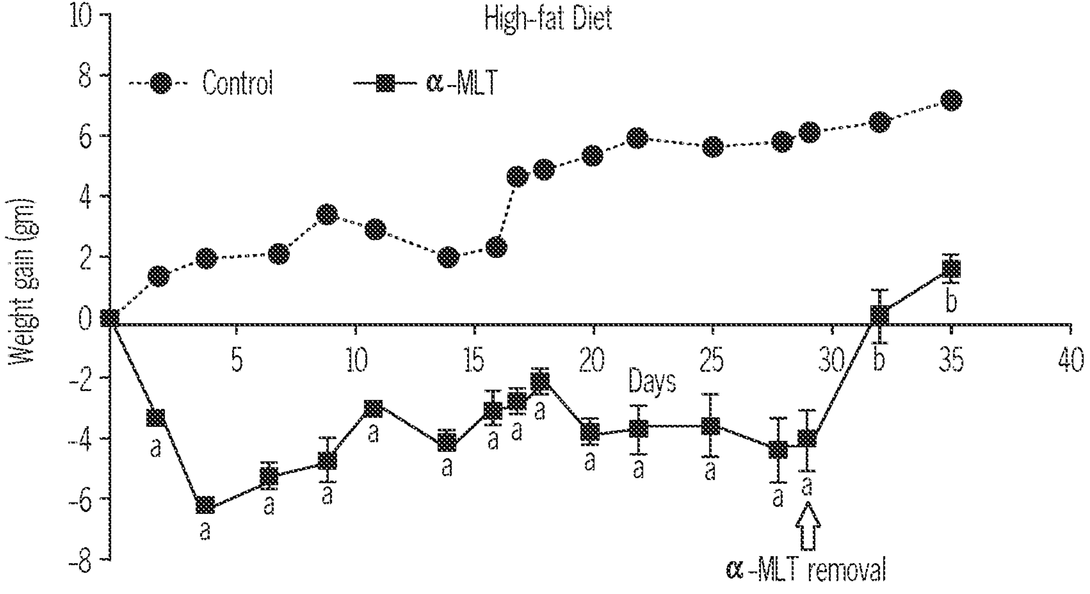

Next, Applicant examined the effect of α-MLT on the body weight in WT C57BL/6 male mice on a normal diet or a high-fat diet (55% calories from fat). The drug was given in drinking water (1 mg/ml). Both with the normal diet and the high-fat diet, mice gained weight when not treated with α-MLT (FIGS. 2A-B). In contrast, the mice treated with α-MLT showed a decrease in body weight (FIGS. 2A-B). This weight-reducing effect was evident with both diets.

Figure 2C:
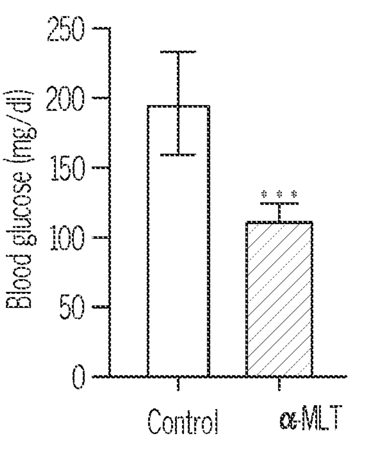
Figure 2C:
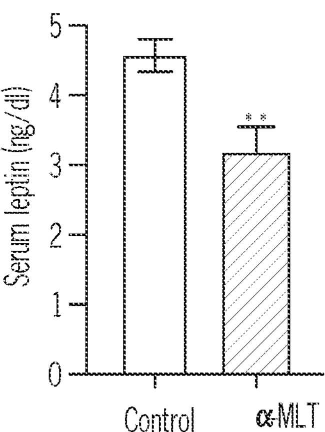
Figure 2D:
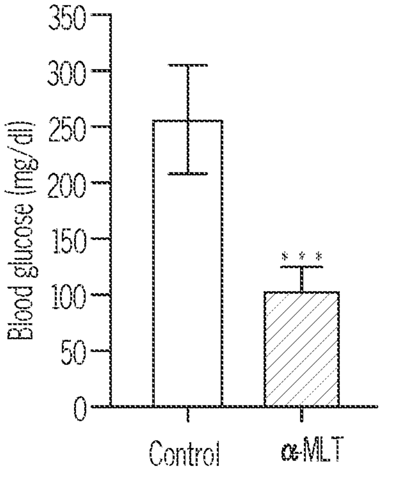
Figure 2D:
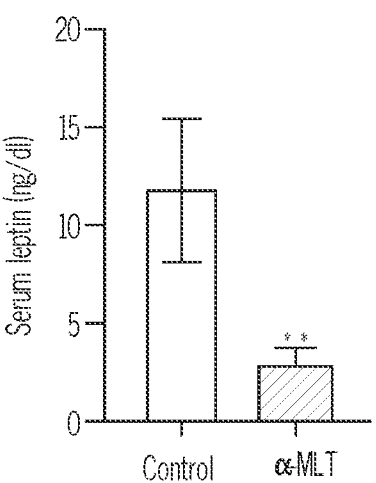

Applicant was also able to show that the effect of the drug is reversible. When the drug was withdrawn, mice began to gain weight (FIG. 2B). At 4-weeks of drug exposure, circulating levels of glucose and leptin were measured. Blood glucose was higher in control (i.e., untreated) mice on the high-fat diet than in those on the normal diet (FIGS. 2C-2D). The same was true with leptin levels, which correspond to fat content (FIGS. 2C-2D).

Figure 3A:
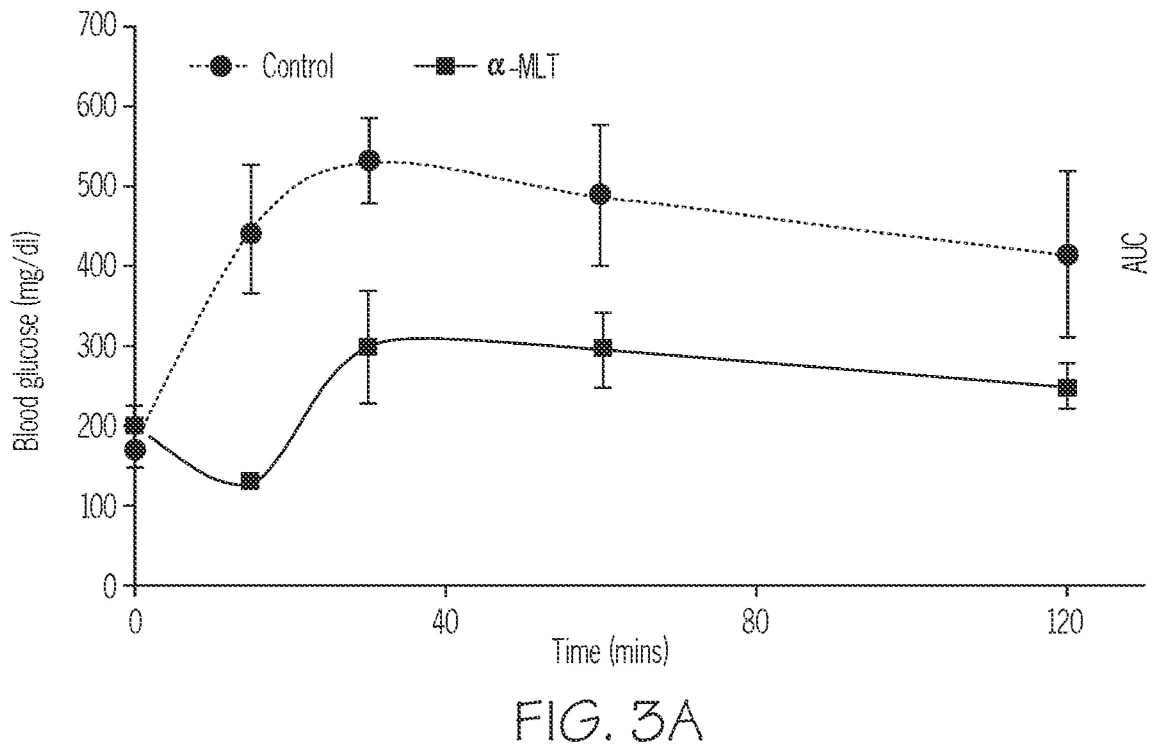
FIGS. 3A-E illustrate the impact of α-MLT on glucose tolerance test, liver and abdominal fat weight, and hepatic steatosis in wild type mice on a high-fat diet. Wild type male mice were fed with HFD for 12 weeks and then the mice were divided into two groups. One group of mice received α-MLT (1 mg/ml in drinking water) ad libitum for 3 weeks and the other group received drinking water alone ad libitum. At the end of 2 weeks, blood glucose was measured following 4-h fasting and then the intraperitoneal glucose tolerance test was performed (FIGS. 3A-B). The diet and α-MLT administration continued another week; then the mice were killed, and the weights of liver and abdominal fat pad were determined (FIGS. 3C-D). Liver tissue was fixed and stained with Oil-O-red for neutral lipids (63×) (FIG. 3E). Data means±S. E. M (N=5 mice/group). *, p<0.05; ***, p<0.001.
Figure 3B:
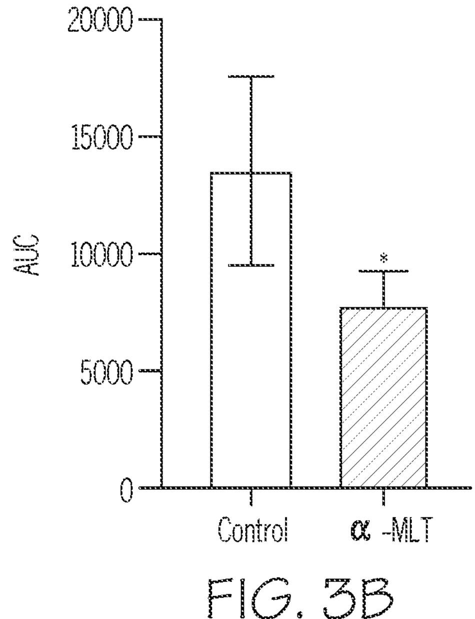
Figure 3C:
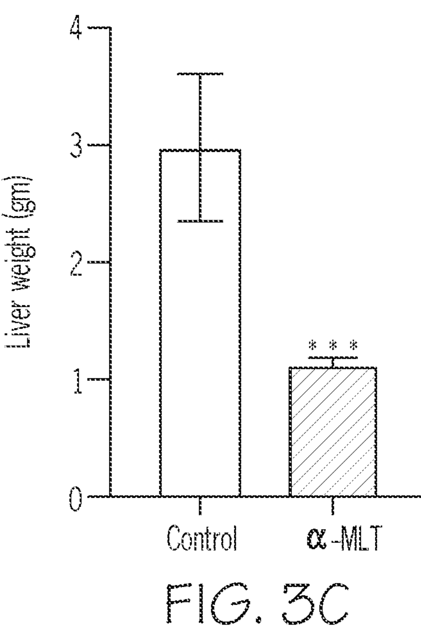
Figure 3D:
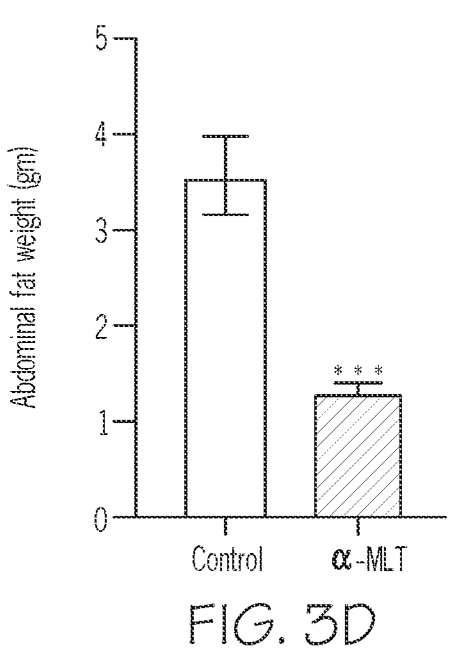

In mice treated with α-MLT, there was a significant decrease in circulating levels of glucose and leptin (FIGS. 2C-2D). These changes were seen in response to the drug independent of the diet. Applicant then performed glucose-tolerance test in control and α-MLT-treated (2-week treatment; 1 mg/ml in drinking water) mice which were fed the high-fat diet for 12 weeks. The mice on α-MLT showed better glucose tolerance, indicative of improved insulin sensitivity (FIGS. 3A-B). At the end of the experiment, mice were killed, and liver and abdominal fat pad were excised and weighed. Treatment with α-MLT reduced the weight of the liver and the abdominal fat (FIGS. 3C-D).

Figure 3E:
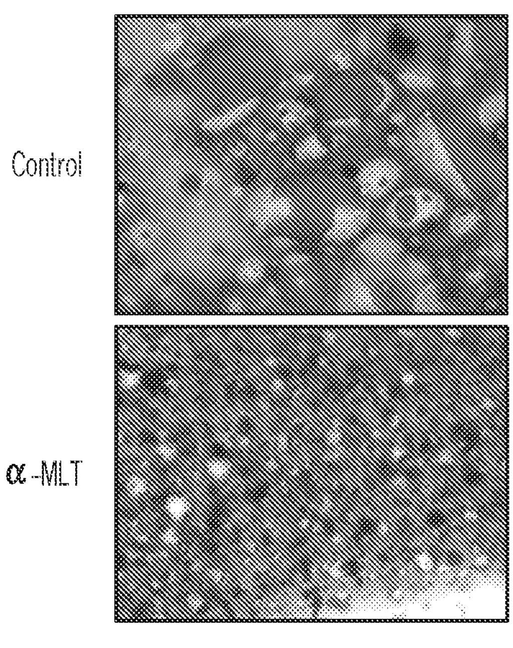

Example 1.11. Prevention of Hepatic Steatosis by α-MLT in Wild Type Mice on a High-Fat Diet Wild type mice developed fatty liver when fed a high-fat diet for 14 weeks as evident from Oil-red-O staining of the liver sections for neutral lipids (FIG. 3E). The hepatic steatosis was almost completely prevented by α-MLT treatment during the last two weeks of this 14-week period (FIG. 3E). In this experiment, mice were fed the high-fat diet for 12-weeks, after which the mice were divided into two groups, one with no α-MLT exposure and the other with α-MLT administration. The drug treatment was continued for two additional weeks, and all through the experiment, both groups were continuously fed the same high-fat diet.

Example 1.12. Effect of α-MLT on Body Weight in Female Mice on a Normal Diet

The experiments described above were done with male mice. To see if α-MLT elicits a similar weight-loss effect in female mice, wild type female mice were exposed to α-MLT (1 mg/ml in drinking water) at 3 months of age. The untreated mice gained weight and α-MLT-exposed mice lost weight (FIG. 4A). At end of 2 weeks treatment, mice were killed and mammary fat pad and liver were excised and weighed. The weights of both tissues decreased in the treated mice (FIGS. 4B-C). Blood glucose levels and serum leptin levels were also decreased in the treated mice (FIGS. 4D-E). These data confirm the weight-reducing effect of α-MLT in both males and females.

Figure 5A:
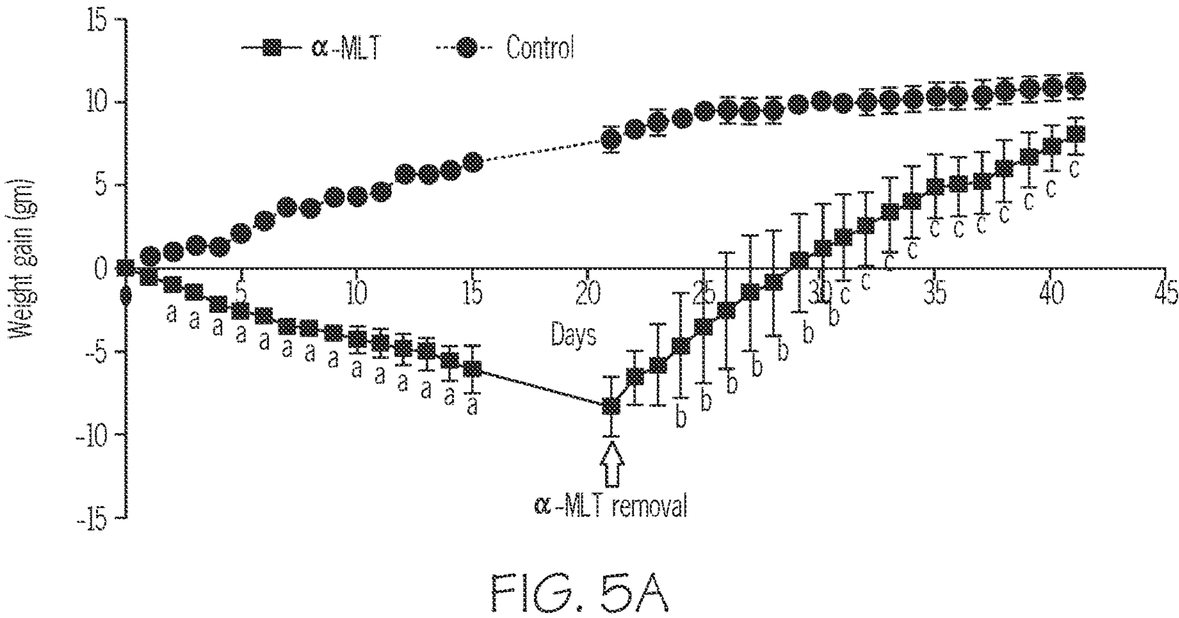
FIGS. 5A-C illustrate the effect of α-MLT on body weight and its reversibility in oblob mice on a normal diet. oblob male mice (3-month-old) were exposed to drinking water alone or to α-MLT (1 mg/ml) in drinking water. Body weight was measured throughout the experiment (FIG. 5A). After three weeks of treatment, mice were killed, and the weights of the liver (FIG. 5B) and abdominal fat pad (FIG. 5C) were determined. Data are means±S. E. M (N=5 mice/group). *, p<0.05; *, p<0.001. To assess the reversibility of α-MLT effect, the drug was withdrawn in the treatment group after 3-week treatment period, and the monitoring of the body weight continued for an additional 3 weeks (FIG. 5**A). a, p<0.001 compared to the control group; b, p<0.01 and c, p<0.001 compared to the body weight on the day of the drug withdrawal.
Figure 5B:
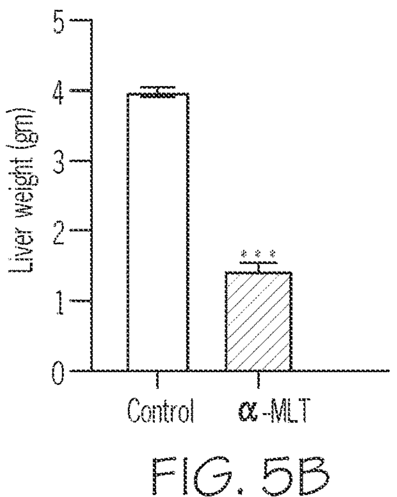
Figure 5C:
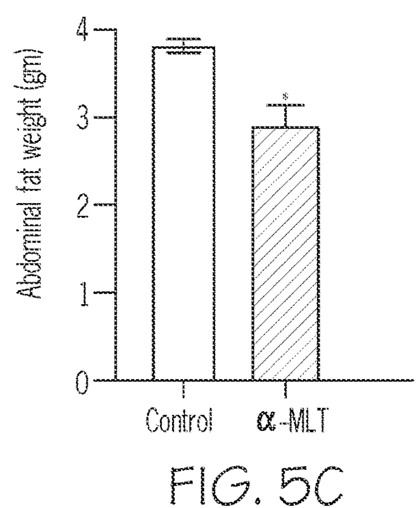

Example 1.13. Effect of α-MLT in Oblob Mice on a Normal Diet oblob mice are deficient in leptin and therefore obese even on a normal diet. These mice exhibit increased food intake, insulin resistance, and elevated blood glucose. oblob mice on normal diet are widely used as a model for diabetes and obesity. Applicant used 12-week-old male oblob mice to evaluate the weight-reducing effect of α-MLT (1 mg/ml in drinking water). There was a gradual weight gain on a normal diet in control mice without the drug (FIG. 5A). In contrast, mice exposed to α-MLT lost weight. At the end of 3-week drug exposure, the reversibility of α-MLT effect was evaluated by withdrawing the drug. The animals started gaining weight upon the drug withdrawal. At the end of the three-week treatment with α-MLT, mice were killed and the weights of the liver and abdominal fat pad were determined. The treatment with the drug significantly reduced the liver weight (FIG. 5B) and abdominal fat (FIG. 5C).

Figure 6A:
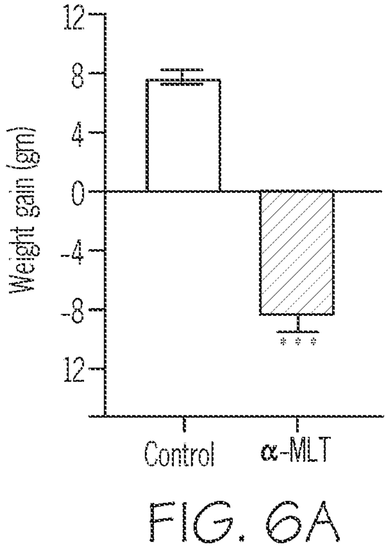
FIGS. 6A-E illustrate the effects of α-MLT on body weight and other biological parameters in oblob mice on a normal diet. Twelve-week-old oblob male mice were administered either drinking water alone or α-MLT (1 mg/ml) in drinking water. Body weight (FIG. 6A) and food intake (FIG. 6B) were measured daily. After three weeks of this treatment regimen, blood glucose (FIG. 6C) was measured and the intraperitoneal glucose tolerance test (FIGS. 6D-E) was performed. Data are means±S. E. M (N=5 mice/group). *, p<0.05; ***, p<0.001.
Figure 6B:
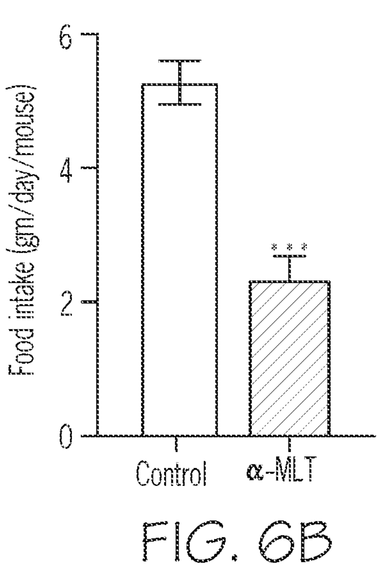
Figure 6C:
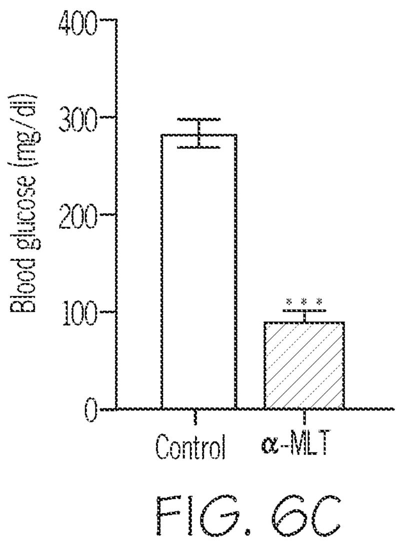
Figure 6D:
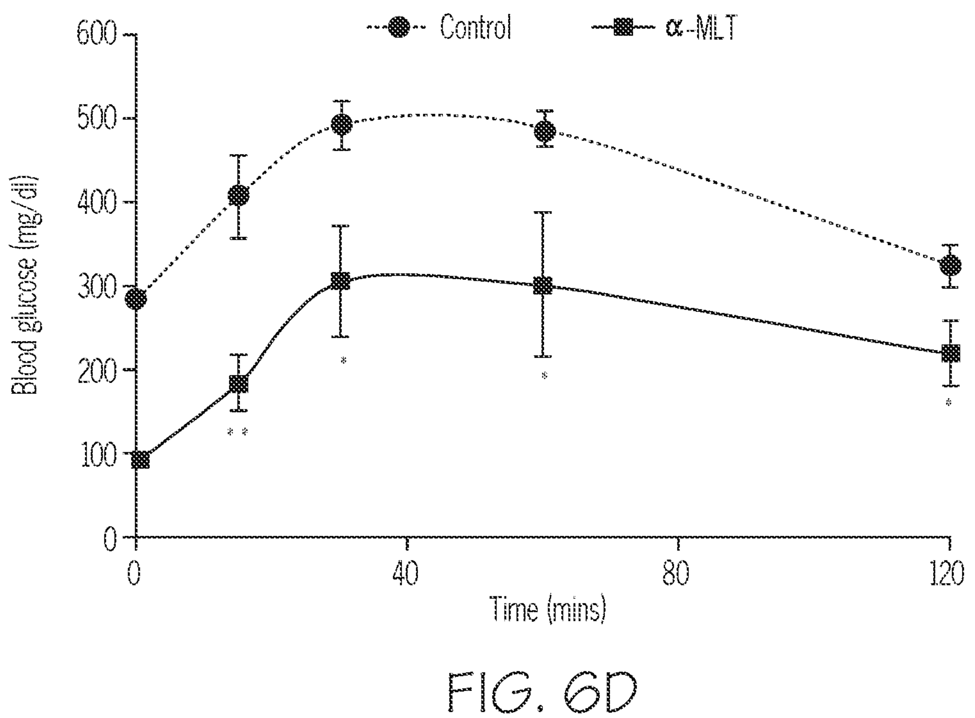
Figure 6E:
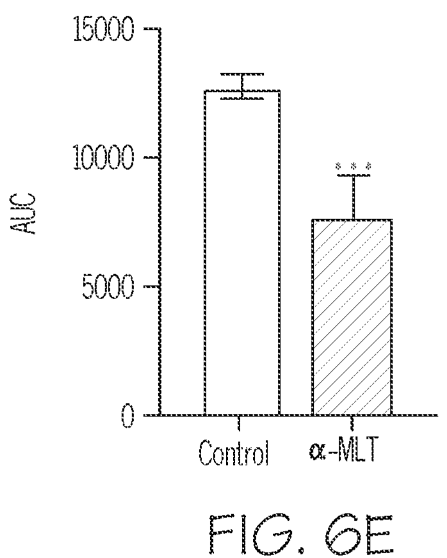

Applicant also monitored food intake, blood glucose, and glucose tolerance in control mice and α-MLT-treated mice. Applicant found that: (i) body weight increased in mice without α-MLT whereas body weight decreased in mice exposed to the drug (FIG. 6A); (ii) α-MLT decreased food intake (FIG. 6B); (iii) blood glucose was lower in mice exposed to α-MLT (FIG. 6C); and (iv) α-MLT improved insulin sensitivity as seen with glucose tolerance test (FIGS. 6D-E).

Example 1.14. Serum Biochemical Profile in Response to α-MLT Treatment in Wild Type Mice on a High-Fat Diet Applicant evaluated the serum profile for metabolites and enzymes to assess the impact of α-MLT (4 weeks treatment; 1 mg/ml in drinking water) in normal mice which were on the high-fat diet for three months prior to initiation of the drug treatment. These tests were designed to assess the function of the kidneys and liver. Plasma lipid profile indicated no significant change in triglycerides, but a significant decrease in cholesterol levels (Table 1).

TABLE 1

Effect of α-MLT treatment (1 mg/ml in drinking water for 4 weeks) on serum lipid profile, kidney function and liver function in wild type mice on the high-fat diet. At the end of the treatment period, blood was collected from control (i.e., untreated) and treated mice to prepare serum, which was used for analysis. Values are means ± S.E.M (N = 5 mice/group).

| | Control | Treated | p value |
|---|---|---|---|
| Lipid Profile | | | |
| Cholesterol (mg/dl) | 145 ± 4 | 106 ± 3 | 0.0001 |
| Triglycerides (mg/dl) | 73 ± 5 | 97 ± 17 | 0.1 |

TABLE 1-continued

Effect of α-MLT treatment (1 mg/ml in drinking water for 4 weeks) on serum lipid profile, kidney function and liver function in wild type mice on the high-fat diet. At the end of the treatment period, blood was collected from control (i.e., untreated) and treated mice to prepare serum, which was used for analysis. Values are means ± S.E.M (N = 5 mice/group).

| | | | |
|---|---|---|---|
| Kidney Function | | | |
| BUN (mg/dl) | 28.6 ± 2.9 | 34.2 ± 2.6 | 0.1 |
| Creatinine (mg/dl) | 0.25 ± 0.03 | 0.30 ± 0.04 | 0.2 |
| Liver Function | | | |
| Total protein (g/dl) | 4.78 ± 0.09 | 4.25 ± 0.06 | 0.001 |
| Albumin (g/dl) | 2.25 ± 0.05 | 1.90 ± 0.04 | 0.001 |
| Globulin (g/dl) | 2.53 ± 0.05 | 2.35 ± 0.09 | 0.06 |

| Amino acids | WT-HFD WT-HFD-α-MLT | p value | ob/ob-ND ob/ob-ND-α-MLT | p value |
|---|---|---|---|---|
| AST (U/I) | 70.5 ± 7.0 | | 79.5 ± 16.3 | 0.32 |
| Total bilirubin (mg/dl) | 0.5 ± 0.1 | | 0.6 ± 0.1 | 0.56 |

High-fat diet caused a marked increase in liver weight, and the treatment with α-MLT reversed this effect. Accordingly, there was a small, but significant, decrease in plasma albumin levels. There was however no compromise in liver function as evident from normal levels of bilirubin and the enzyme aspartate transaminase (glutamate-oxaloacetate transaminase) (AST).

The same was true with the kidney function. There was no evidence of compromise in kidney function as seen with the data on blood urea nitrogen and blood creatinine.

Example 1.15. Plasma Amino Acid Profile in Response to α-MLT Treatment

For the determination of plasma amino acids, Applicant had two mouse models of obesity: wild type mice fed the high-fat diet for 12 weeks and 12-week-old oblob mice fed with the normal diet. In both models, the treatment with α-MLT was for 2 weeks. At the end of this period, mice were killed and blood collected. Plasma levels of amino acids were then determined in all four groups: wild type mice with no α-MLT, wild type mice with α-MLT; oblob mice with no α-MLT; oblob mice with α-MLT. The data are given in Table 2.

TABLE 2

Plasma concentration of amino acids in high-fat diet (HFD)-fed C57BL/6 mice and normal diet (ND)-fed oblob mice with and without α-MLT treatment. Values are given as nmoles/ml (μM) in plasma (means ± S.D; 3 mice/group).

| | | | | | | |
|---|---|---|---|---|---|---|
| Taurine | 519.08 ± 32 | 506.98 ± 22 | 0.280 | 878.32 ± 118 | 610.13 ± 40 | 0.010 |
| Aspartic acid | 15.78 ± 2 | 15.06 ± 2 | 0.294 | 19.88 ± 4 | 8.13 ± 1 | 0.004 |
| Threonine | 302.73 ± 70 | 284.15 ± 10 | 0.309 | 185.88 ± 30 | 196.92 ± 11 | 0.292 |
| Serine | 182.91 ± 25 | 150.56 ± 8 | 0.025 | 186.45 ± 46 | 123.75 ± 6 | 0.041 |
| Asparagine | 68.54 ± 13 | 48.18 ± 9 | 0.214 | 87.02 ± 37 | 39.78 ± 4 | 0.018 |
| Glutamine | 767.74 ± 50 | 712.05 ± 32 | 0.063 | 853.17 ± 179 | 669.6 ± 32 | 0.013 |
| Glycine | 210.49 ± 35 | 144.63 ± 14 | 0.006 | 206.88 ± 54 | 140.7 ± 8 | 0.050 |
| Alanine | 502.99 ± 55 | 468.31 ± 67 | 0.227 | 721.18 ± 194 | 466.4 ± 15 | 0.043 |
| Citrulline | 60.63 ± 12 | 56.4 ± 6 | 0.272 | 73.37 ± 10 | 82.73 ± 9 | 0.151 |
| Valine | 318.23 ± 50 | 304.66 ± 27 | 0.323 | 249.57 ± 45 | 216.97 ± 28 | 0.174 |
| Methionine | 102.63 ± 30 | 98.7 ± 27 | 0.426 | 85.18 ± 10 | 87.06 ± 26 | 0.456 |
| Isoleucine | 115.98 ± 13 | 104.25 ± 8 | 0.092 | 104.38 ± 23 | 78.42 ± 13 | 0.085 |
| Leucine | 168.20 ± 23 | 163.15 ± 15 | 0.364 | 278.42 ± 45 | 224.92 ± 34 | 0.088 |
| Tyrosine | 103.3 ± 22 | 120.39 ± 17 | 0.132 | 121.65 ± 9 | 94.68 ± 25 | 0.074 |
| Phenylalanine | 88.35 ± 3 | 89.86 ± 15 | 0.426 | 132.85 ± 9 | 108.9 ± 15 | 0.041 |
| Ornithine | 115.44 ± 25 | 48.9 ± 2 | 0.001 | 172.83 ± 23 | 97.75 ± 22 | 0.007 |
| Lysine | 446.44 ± 66 | 402.98 ± 29 | 0.135 | 289.35 ± 62 | 306.73 ± 52 | 0.364 |
| 1-Methylhistidine | 4.65 ± 0.5 | 4.23 ± 0.5 | 0.099 | 6.77 ± 1.6 | 8.71 ± 1.4 | 0.096 |

TABLE 2-continued

Plasma concentration of amino acids in high-fat diet (HFD)-fed C57BL/6 mice and normal diet (ND)-fed oblob mice with and without α-MLT treatment. Values are given as nmoles/ml (μM) in plasma (means ± S.D; 3 mice/group).

| | | | | | | |
|---|---|---|---|---|---|---|
| Histidine | 87.23 ± 4 | 88.04 ± 4 | 0.394 | 97.55 ± 10 | 90.4 ± 10 | 0.209 |
| Tryptophan | 112.60 ± 12 | 6.06 ± 12 | 0.000 | 121.72 ± 15 | 24.53 ± 29 | 0.003 |
| Arginine | 71.64 ± 38 | 124.36 ± 12 | 0.018 | 46.73 ± 7 | 94.42 ± 20 | 0.008 |
| Proline | 180.41 ± 57 | 173.99 ± 17 | 0.419 | 194.62 ± 33 | 137.93 ± 19 | 0.031 |

In wild type mice on the high-fat diet, treatment with α-MLT reduced the plasma levels of serine, glutamine, glycine, tryptophan, and ornithine. The levels of other amino acids were not altered. In oblob mice with the normal diet, treatment with α-MLT caused a significant decrease in a broader spectrum of amino acids: taurine, aspartate, serine, asparagine, glutamine, glycine, alanine, phenylalanine, tryptophan, proline, and ornithine. This list includes all 6 amino acids whose levels were altered in wild type mice. The most robust decrease occurred with tryptophan in both models. Interestingly, the plasma levels of arginine increased in both models.

Example 1.16. Discussion

In this Example, Applicant has identified the tryptophan derivative α-methyl-L-tryptophan (α-MLT) as an effective and reversible weight-loss agent. The compound is orally active and efficacious in different mouse models of obesity, both dietary and genetic. α-MLT is already in use in humans as a tracer to evaluate the health of serotonergic neurons in the brain. The rationale for this use is that α-MLT crosses the blood-brain barrier, gets taken up into serotonergic neurons, and is converted into α-methylserotonin via the tryptophan hydroxylase pathway that is selective for serotonergic neurons in the brain.

In this Example, α-MLT was given orally in drinking water and thus the animals were exposed to the drug continuously. With an estimate that mice drink ~4 ml water per day, the drug dose used in the present study (1 mg/ml of the L-isomer) translates to approximately 0.13 mg/day/g body weight). The weight-reducing effect of the drug was observed within a day of the drug administration. Moreover, Applicant observed that only the L-isomer is pharmacologically active and that the efficacy of the compound as a weight-loss agent is evident in multiple models of obesity in mice.

Furthermore, the effect of α-MLT on body weight is reversible. Mice resume weight gain immediately upon withdrawal of the drug. It is orally active and the effect is seen at a dose of 1 mg/ml in drinking water. Additionally, the weight-loss effect is associated with decreased food intake.

Without being bound by theory, Applicant envisions that the molecular mechanism by which α-MLT reduces food intake and body weight most likely involves the effect mediated by α-methylserotonin as a satiety signal in the brain. It is well known that α-MLT crosses the blood-brain barrier and gets converted into α-methylserotonin as evident from its use in clinics as a probe to monitor the health of serotonergic neurons. It is also known that α-methylserotonin serves as an agonist for serotonin receptors, particularly for the 5HT2 receptor subtype and that activation of 5HT2 receptor controls appetite. Nonetheless, elucidation of the exact molecular mechanism underlying the weight-loss effect of α-MLT requires further investigation.

The changes in the plasma amino acid profile in response to α-MLT treatment are interesting. The primary change is a decrease in the concentrations of certain specific amino acids. This could be explained to a major extent based on the fact that α-MLT is a blocker of the broad-specific amino acid transporter SLC6A14, which is expressed highly in the ileum and colon. The substrates for SLC6A14 include all of the neutral amino acids as well as the cationic amino acids. It is possible that the transport function of SLC6A14 contributes to absorption of these amino acids, derived from either diet or colonic bacteria. Therefore, chronic exposure to α-MLT in drinking water is expected to interfere with this absorption process, thus leading to a decrease in the plasma levels of specific amino acids. It is important to note however that the decrease in tryptophan levels is much more marked than the decrease in other amino acids, suggesting additional mechanisms, at least for this particular amino acid.

α-MLT has been shown to be effective for the treatment of cancers that are associated with upregulation of the amino acid transporter SLC6A14. However, the weight-loss effect of the compound is independent of its ability to block this transporter as evident from its efficacy to reduce body weight even in Slc6a14-null mice. This suggests that α-MLT is ideal for treatment of obesity-associated cancers. This is particularly so in the case of the estrogen receptor-positive breast cancer, which is promoted by obesity and is also characterized by upregulation of SLC6A14, thus providing two molecular targets for α-MLT (obesity and SLC6A14) to elicit a synergistic therapeutic effect. α-MLT would also be useful in the treatment of other obesity-related health problems such as diabetes, hypertension, cardiovascular diseases, and fatty liver.

Based on these pharmacologic features of α-MLT, there is potential for this compound as an anti-obesity drug in humans. In preclinical animal models, α-MLT given orally at a dose of 150 mg/kg per day showed no noticeable adverse effects in rats. Applicant's studies have shown that at a daily dose of 1 mg/ml in drinking water, which translates approximately to 115 mg/kg (the average daily water intake in male C57BL/6 mice, 4 ml/30 g body weight), there was no evidence of significant changes in liver function and kidney function. The dose of 115 mg/kg in mice approximates to 1 g of the drug in humans with body weight of 70 kg, a practically feasible dose for use in humans. As such, the findings of the present study provide a strong rationale and scientific basis for a more detailed evaluation of α-MLT as an anti-obesity drug in preclinical animal models and for subsequent clinical trials in humans.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating a condition in a subject, said method comprising:

administering to the subject a composition comprising alpha-methyl-L-tryptophan, wherein the alpha-methyl-L-tryptophan is administered at a concentration sufficient to treat the condition in the subject, and wherein the condition is selected from the group consisting of hyperglycemia, diet-induced diabetes, high-fat diet-induced diabetes, insulin resistance, metabolic syndrome, extra weight, obesity, hepatic steatosis, and combinations thereof.

2. The method of claim 1, wherein the alpha-methyl-L-tryptophan is in an enantiomerically pure form.

3. The method of claim 1, wherein the alpha-methyl-L-tryptophan is in a non-racemic form.

4. The method of claim 1, wherein D isomers of tryptophan are at concentrations of less than 5 wt %.

5. The method of claim 1, wherein D isomers of tryptophan are at concentrations of less than 1 wt %.

6. The method of claim 1, wherein the composition lacks D isomers of tryptophan.

7. The method of claim 1, wherein the alpha-methyl-L-tryptophan is administered at a concentration of at least 0.1 mg/g body weight/day.

8. The method of claim 1 wherein the composition further comprises Carbidopa.

9. The method of claim 1, wherein the composition is in the form of a liquid.

10. The method of claim 9, wherein the alpha-methyl-L-tryptophan is dissolved in the liquid at a concentration of at least 1 mg/ml.

11. The method of claim 1, wherein the method is used to treat the condition.

12. The method of claim 1, wherein the subject is a human being.

13. The method of claim 1, wherein the condition is extra weight, and wherein the composition treats the extra weight in the subject.

14. The method of claim 1, wherein the subject is obese, and wherein the composition treats the obesity in the subject.

15. The method of claim 1, wherein the composition acts by reducing food intake in the subject.

16. The method of claim 1, further comprising a step of instructing the subject to administer the composition in order to treat the condition in the subject.

17. The method of claim 1, wherein the administering occurs by a method selected from the group consisting of intravenous administration, intramuscular administration, intradermal administration, intraperitoneal administration, subcutaneous administration, spray-based administration, aerosol-based administration, in ovo administration, oral administration, intraocular administration, intratracheal administration, intranasal administration, inhalational administration, and combinations thereof.

18. The method of claim 1, wherein the administering occurs by oral administration.

19. The method of claim 18, wherein the orally administered composition is in liquid form, and wherein the alpha-methyl-L-tryptophan is in a non-racemic form.

* * * * *